(12) United States Patent
Teixeira et al.

(10) Patent No.: US 8,974,399 B2
(45) Date of Patent: Mar. 10, 2015

(54) SYSTEM AND METHOD FOR SAMPLING DEVICE FOR BODILY FLUIDS

(71) Applicant: Avent, Inc., Alpharetta, GA (US)

(72) Inventors: Scott M. Teixeira, Cumming, GA (US); Andrew T. Baker, Norcross, GA (US); Brian J. Cuevas, Cumming, GA (US); Adrienne A. Hershey, Cumming, GA (US); Kok-Ming Tai, Lawrenceville, GA (US); Benone Tarcau, Lawrenceville, GA (US); Joseph A. Cesa, Cumming, GA (US); Amy G. Williams, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 13/941,825

(22) Filed: Jul. 15, 2013

(65) Prior Publication Data

US 2014/0088460 A1    Mar. 27, 2014

Related U.S. Application Data

(62) Division of application No. 13/268,009, filed on Oct. 7, 2011, now abandoned.

(51) Int. Cl.
*A61B 10/00* (2006.01)
*A61B 5/00* (2006.01)
(Continued)

(52) U.S. Cl.
CPC ......... *A61B 10/0051* (2013.01); *A61B 10/0045* (2013.01); *A61B 10/0096* (2013.01);
(Continued)

(58) Field of Classification Search
USPC ............. 128/205.29; 600/562, 563, 573, 581; 604/19, 35, 93.01, 99.04, 118, 514, 604/516
See application file for complete search history.

(56) References Cited

U.S. PATENT DOCUMENTS

| | | |
|---|---|---|
| 3,518,164 A | 6/1970 | Andelin |
| 4,283,498 A | 8/1981 | Schlesinger |

(Continued)

FOREIGN PATENT DOCUMENTS

| | | |
|---|---|---|
| EP | 0 300 221 A2 | 1/1989 |
| EP | 1 234 543 A1 | 8/2002 |

(Continued)

OTHER PUBLICATIONS

Koper, J. W. et al, "Prevention of Cross-Reactions in the Enzyme Linked Immunosorbent Assay (Elisa) for the Detection of *Staphylococcus aureus* Enterotoxin Type B in Culture Filtrates and Foods," Journal of Food Safety, vol. 2, No. 1, Jan. 1, 1980, pp. 35-45.

(Continued)

*Primary Examiner* — Max Hindenburg
*Assistant Examiner* — Jonathan M Foreman
(74) *Attorney, Agent, or Firm* — Dority & Manning, P.A.

(57) ABSTRACT

There is provided a device for sampling bodily fluids. Some embodiments have a handle, a lumen, and a diverter valve. The distal end of the handle is adapted to connect with a sampling device and is in fluid communication with the lumen. There is a vacuum connection on the proximal end of the handle that is also in fluid communication with the lumen. A suction valve may desirably be located in the lumen to control the application of vacuum from the vacuum connection to the sampling device. The diverter valve directs the flow through the lumen such that a sample from the patient goes into a sputum trap when the trap is connected. The device may further have a saline port in fluid communication with the lumen, located distal to the suction valve, for rinsing the tube and diluting secretions.

3 Claims, 12 Drawing Sheets

(51) Int. Cl.
  *A61B 1/00* (2006.01)
  *A61B 1/267* (2006.01)
  *A61M 1/00* (2006.01)

(52) U.S. Cl.
  CPC .......... *A61M1/0043* (2013.01); *A61B 1/00094* (2013.01); *A61B 1/2676* (2013.01); *A61M 1/0005* (2013.01); *A61M 1/0023* (2013.01)
  USPC ......................................... 600/562; 600/573

(56) References Cited

U.S. PATENT DOCUMENTS

| | | | |
|---|---|---|---|
| 4,465,485 A | 8/1984 | Kashmer et al. | |
| 4,586,491 A | 5/1986 | Carpenter | |
| 4,643,197 A * | 2/1987 | Greene et al. | 600/575 |
| 4,827,944 A | 5/1989 | Nugent | |
| 4,932,081 A | 6/1990 | Burns | |
| 4,961,432 A | 10/1990 | Guirguis | |
| 5,135,490 A | 8/1992 | Strickland | |
| 5,165,420 A | 11/1992 | Strickland | |
| 5,246,012 A | 9/1993 | Strickland | |
| 5,363,860 A | 11/1994 | Nakao et al. | |
| 5,433,195 A | 7/1995 | Kee et al. | |
| 5,595,187 A | 1/1997 | Davis | |
| 5,685,843 A | 11/1997 | Enhorning | |
| 5,846,183 A | 12/1998 | Chilcoat | |
| 5,919,174 A | 7/1999 | Hanson | |
| 6,325,785 B1 | 12/2001 | Babkes et al. | |
| 6,361,505 B1 | 3/2002 | Rainen et al. | |
| 6,375,625 B1 | 4/2002 | French et al. | |
| 6,398,775 B1 | 6/2002 | Perkins et al. | |
| 6,429,026 B1 | 8/2002 | Pettersson et al. | |
| 6,632,842 B2 | 10/2003 | Chaudry et al. | |
| 6,679,264 B1 | 1/2004 | Deem et al. | |
| 7,018,330 B2 | 3/2006 | Alekseenko et al. | |
| 7,160,248 B2 | 1/2007 | Alekseenko et al. | |
| 7,270,959 B2 | 9/2007 | Hudak | |
| 7,384,793 B2 | 6/2008 | McCash et al. | |
| 7,517,495 B2 | 4/2009 | Wu et al. | |
| 7,527,058 B2 | 5/2009 | Wright et al. | |
| 8,021,873 B2 | 9/2011 | Johnson et al. | |
| 8,177,760 B2 * | 5/2012 | Rome et al. | 604/247 |
| 2002/0123697 A1 | 9/2002 | Ishizaka et al. | |
| 2004/0014203 A1 | 1/2004 | Wickstead et al. | |
| 2004/0228764 A1 | 11/2004 | Stephens et al. | |
| 2005/0272975 A1 | 12/2005 | McWeeney et al. | |
| 2006/0074347 A1 | 4/2006 | Eguchi et al. | |
| 2006/0292035 A1 | 12/2006 | Gould et al. | |
| 2007/0213632 A1 | 9/2007 | Okazaki et al. | |
| 2007/0225559 A1 | 9/2007 | Clerc et al. | |
| 2008/0113391 A1 | 5/2008 | Gibbons et al. | |
| 2008/0199851 A1 | 8/2008 | Egan et al. | |
| 2009/0054809 A1 | 2/2009 | Morishita et al. | |
| 2009/0192448 A1 | 7/2009 | Talamonti | |
| 2009/0301480 A1 | 12/2009 | Elsakka et al. | |
| 2009/0306544 A1 | 12/2009 | Ng et al. | |
| 2009/0306545 A1 | 12/2009 | Elsakka et al. | |
| 2009/0318758 A1 | 12/2009 | Farr et al. | |
| 2010/0016757 A1 | 1/2010 | Greenburg et al. | |
| 2010/0056387 A1 | 3/2010 | Schulz et al. | |
| 2010/0174210 A1 | 7/2010 | Han et al. | |
| 2010/0241091 A1 | 9/2010 | Wu | |
| 2012/0196304 A1 | 8/2012 | Dees et al. | |

FOREIGN PATENT DOCUMENTS

| | | | |
|---|---|---|---|
| EP | | 1 553 394 A1 | 7/2005 |
| EP | | 1 867 973 A1 | 12/2007 |
| WO | WO 92/10971 A1 | | 7/1992 |
| WO | WO 96/39917 A1 | | 12/1996 |
| WO | WO 99/08731 A1 | | 2/1999 |
| WO | WO 02/084266 A2 | | 10/2002 |
| WO | WO 03/105941 A1 | | 12/2003 |
| WO | WO 2004/055516 A1 | | 7/2004 |
| WO | WO 2005/023426 A2 | | 3/2005 |
| WO | WO 2005/026690 A2 | | 3/2005 |
| WO | WO 2005/094665 A2 | | 10/2005 |
| WO | WO 2007/098184 A2 | | 8/2007 |
| WO | WO 2006/055934 A3 | | 1/2008 |
| WO | WO 2007/109418 A3 | | 3/2008 |
| WO | WO 2008/062048 A2 | | 5/2008 |
| WO | WO 2008/085228 A2 | | 7/2008 |
| WO | WO 2007/146613 A3 | | 8/2008 |
| WO | WO 2009/002447 A1 | | 12/2008 |
| WO | WO 2009/018473 A1 | | 2/2009 |
| WO | WO 2009/134634 A3 | | 12/2009 |
| WO | WO 2009/152104 A1 | | 12/2009 |
| WO | WO 2009/152107 A1 | | 12/2009 |
| WO | WO 2009/152119 A1 | | 12/2009 |
| WO | WO 2010/004570 A1 | | 1/2010 |
| WO | WO 2012/150544 A1 | | 11/2012 |
| WO | WO 2014/055995 A1 | | 4/2014 |

OTHER PUBLICATIONS

Li, Chen-Zhong et al., "Paper Based Point-of-Care Testing Disc for Multiplex Whole Cell Bacteria Analysis," Biosensors and Bioelectronics, Elsevier, vol. 26, No. 11, Apr. 21, 2011, pp. 4342-4348.

* cited by examiner

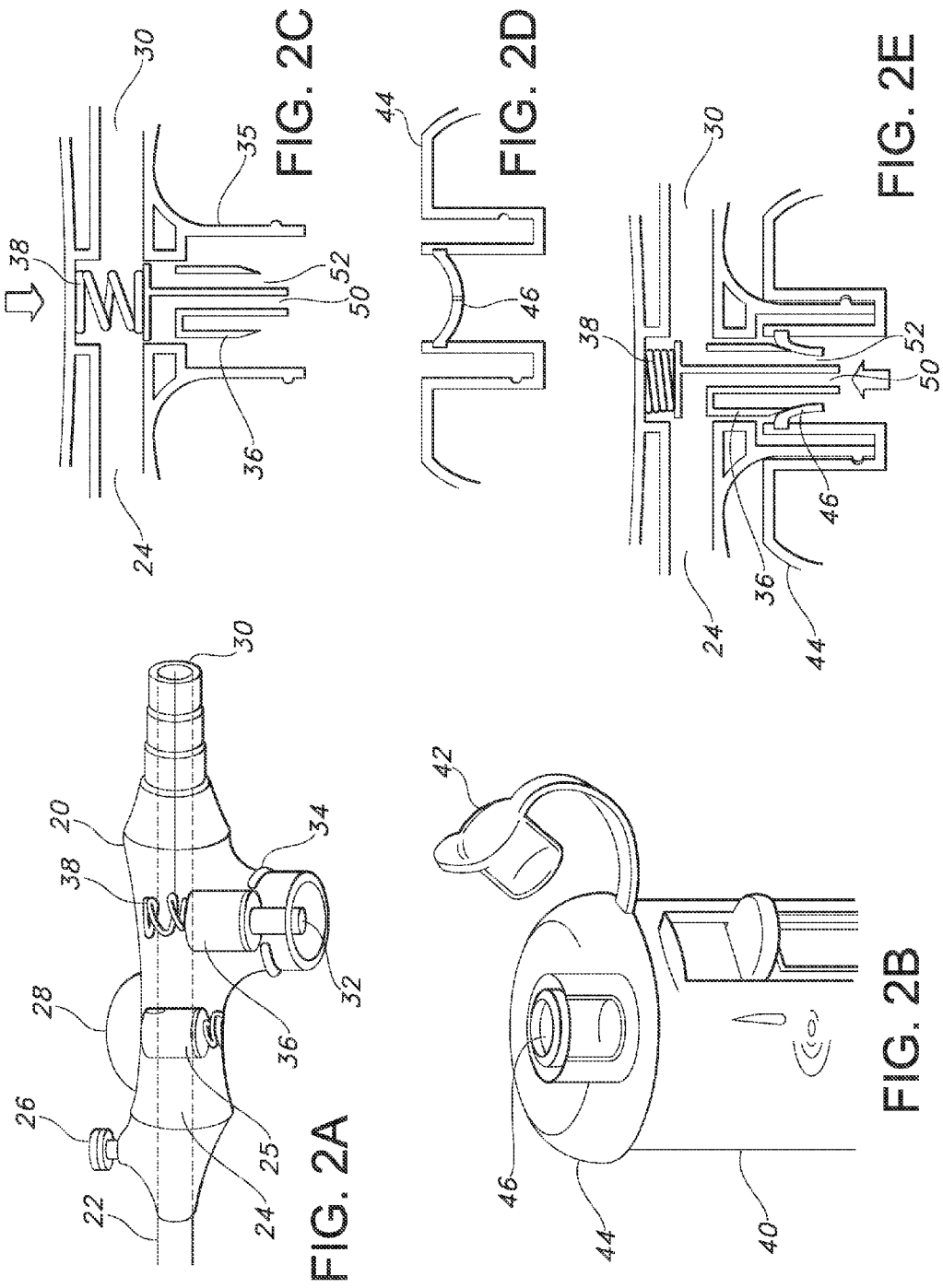

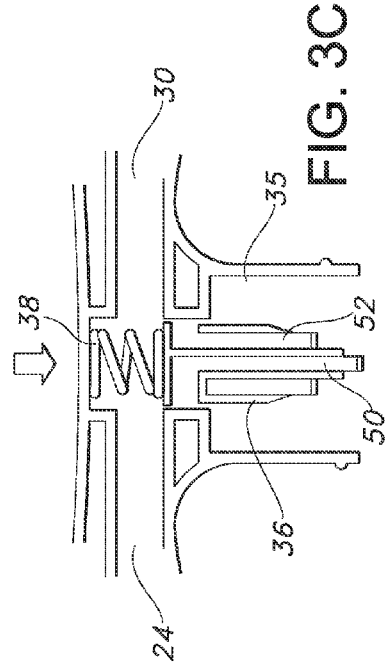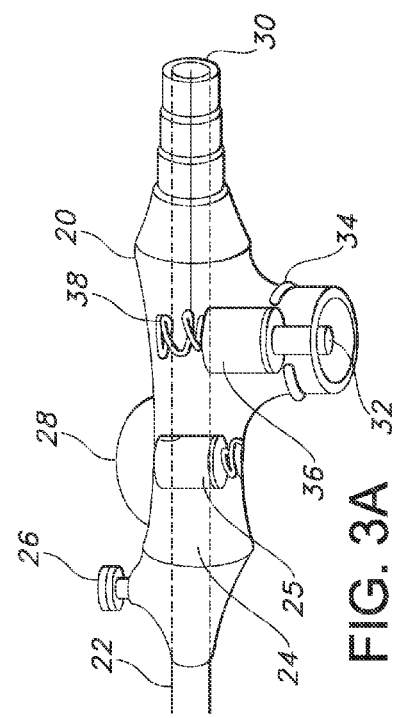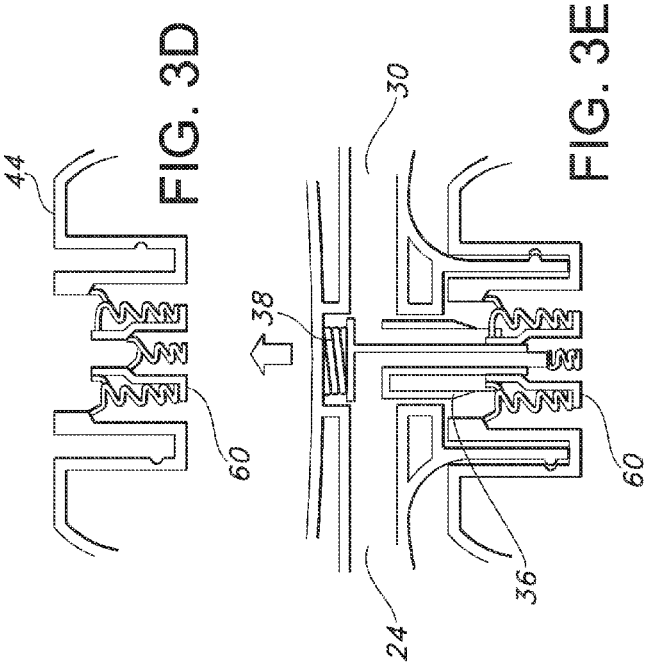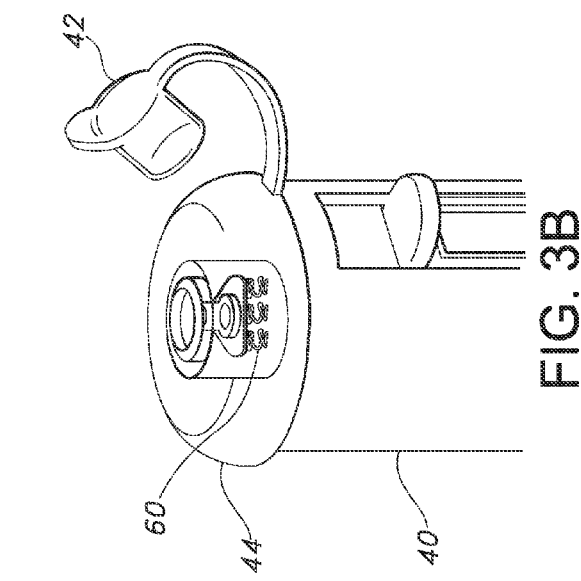

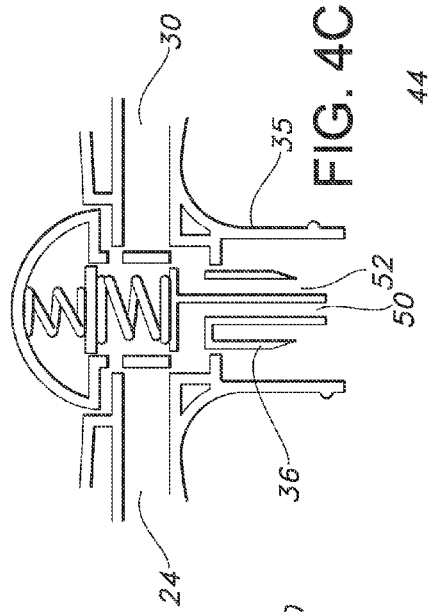
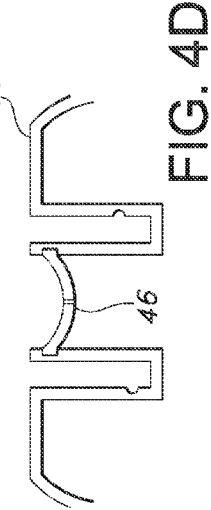
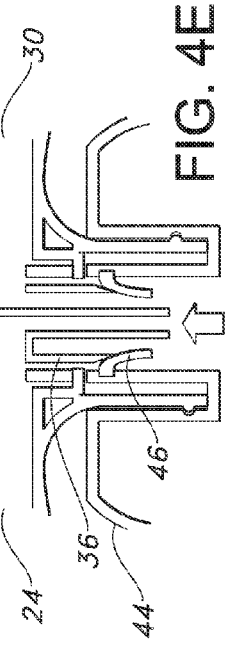
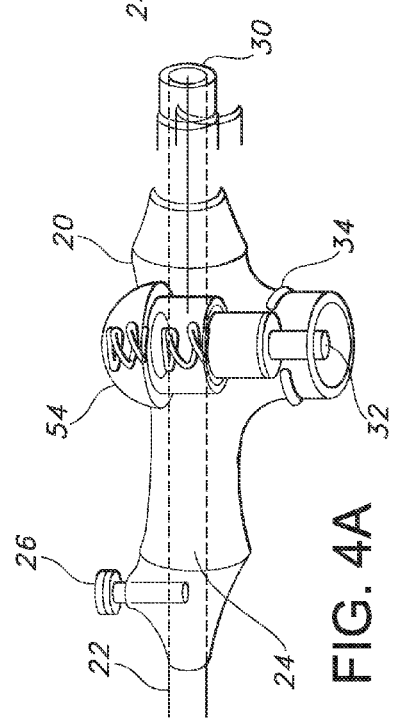
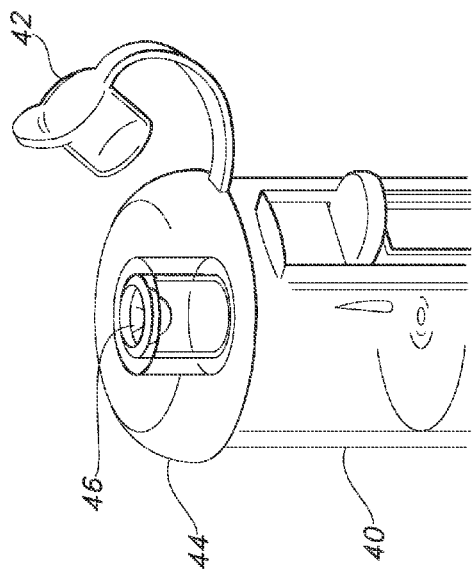

SYSTEM AND METHOD FOR SAMPLING DEVICE FOR BODILY FLUIDS

The present application is a Divisional of U.S. patent application Ser. No. 13/268,009 filed on Oct. 7, 2011 and claims priority thereto.

The present disclosure relates generally to the field of medicine and more particularly relates to obtaining a sample in an integrated system and identifying the bacterial load in that sample specifically in sputum.

When a patient is admitted to a hospital, or a specific unit of the hospital, e.g.; the ICU (intensive care unit), they are often tested for the presence of infection causing microorganisms in their system through blood, urine, skin, and sputum. Depending on hospital protocol this screening test is completed upon admission to the various areas of the hospital or upon clinical signs of infection including fever, increased white blood cell count, discolored sputum, purulent sputum, decreased oxygenation, hazy chest X-ray, etc.

Currently, the sputum samples are obtained via bronchoscopy, non-bronchoscopic broncheoaviolar lavage (BAL), closed suction catheter, open suction catheter, or expectorated sample. The sample is then retained in a separate sputum trap container that is connected to the sampling device through flexible tubing connections or other means (FIG. 1). Current sputum traps are prone to leakage or spillage, causing concern to the medical personnel involved since the exact microorganisms present are unknown. The disconnection of tubing from current sputum traps is also a source for leakage.

The sample in the sputum trap is transported to the clinical microbiology laboratory for microbial testing and analysis. The sputum trap is commonly transported in a pneumatic system from the ICU to the lab. A problem that sometimes arises is that the sample can spill or leak in the pneumatic tubing as it is being transported. This can contaminate the pneumatic system, putting the integrity of other samples transported at risk and requiring a re-sampling of the patient, with its concomitant risks.

While the clinician is waiting for the microbial data to return and the patient is showing clinical signs of infection, common practice is to give the patient 3-5 broad spectrum antibiotics to cover all possible organisms that could be the causing the infection. These antibiotics have toxic side effects to the patient. For example, some antibiotics can cause harm to the function of the kidneys. Overuse of unnecessary antibiotics can cause super bugs and antibiotic resistance, which is a well published universal problem in health care. The use of these potentially unnecessary antibiotics also incurs a large cost to the hospital. The clinician may also isolate a patient that is suspected of having a resistant or highly contagious organism (e.g.; MRSA or TB). There is, of course, an associated cost to so isolate a patient suspected of carrying a concerning organisms.

The first round of microbial data that a physician receives is called a gram stain. A gram stain identifies if a bacterial organism is in either the gram negative or gram positive class and the morphology of the bacteria (i.e. cocci, rod, etc. . . . ). This allows the clinician to remove antibiotic(s) that affect the class of organisms with which the patient is not infected. A gram stain test takes approximately 1 hour to perform, but with transportation time of the sample and the typical lab testing back-log, our results show that most ICU clinicians receive the gram stain results in 12-24 hours. During this time a patient is placed on the 3-5 broad spectrum antibiotics mentioned above until the clinician reviews the gram stain results and removes 1-3 unnecessary broad spectrum antibiotics.

Many studies have tested the specificity and sensitivity of the standard gram stain and the general consensus is that the gram stain in about 80% sensitive and 80% specific. The gram stain is a subjective test because the lab technician is viewing the sample under a microscope to identify the color and location of a staining dye in bacteria cells and tests results could be gram variable, meaning the technician could not identify the bacterial gram class. There are also several steps to complete a gram stain that include chemical washings and dyes that are user dependent. If these steps are not followed well, the test could be less accurate. The gram stain procedure generally includes the followings steps: 1) place a slide with a bacterial smear on a staining rack, 2) stain the slide with crystal violet for 1-2 minutes, 3) pour off the stain, 4) flood slide with Gram's iodine for 1-2 min., 5) pour off the iodine, 6) decolorize by washing the slide briefly with acetone (2-3 seconds), 7) wash slide thoroughly with water to remove the acetone—do not delay with this step, 8) flood slide with safranin counter stain for 2 min., 9) wash with water, 10) blot excess water and dry by hand over (Bunsen) flame.

The second round of microbial data that a physician receives is called a microbial specificity. These results are obtained in 24-48 hours and require culturing of the organisms on an agar plate. Microbial specificity identifies the exact organism(s) that are causing the infection and the concentration of that organism(s) in a quantitative or semi-quantitative fashion. These results allow the clinician to change the broad spectrum antibiotics to antibiotics targeted for the specific organism that is causing the infection. The clinician may also wait to change antibiotics if the patient is improving or until further results are obtained.

The third round of microbial data that a physician received is call antibiotic sensitivities. These results are obtained in 48-72 hours and require testing the cultured sample against known antibiotics to determine the resistance pattern of the organism. Once it is know what antibiotics the organism is sensitive to or will kill the organism(s), the clinician can change to one targeted antibiotic to cure the infection.

Thus, there remains a need in the art for a sampling system that is easy to use and maintains the integrity of the sample, both during sampling and transportation, and that reduces the likelihood that medical personnel with come in contact with the sample. This will improve the quality of the sample and reduce the need for re-sampling of the patient, saving the patient from repeated physical intrusion, saving time in beginning proper treatment and saving money currently used on inappropriate medication.

SUMMARY

In response to the difficulties and problems discussed herein, the present disclosure provides a sampling device for the collection of secretions from a patient. According to the disclosure, a sputum sample is obtained from the patient, desirably below the corina and ideally in the third generation lung lobe. This sample is retained in the sputum trap for transportation to a lab for analysis.

The sampling is done in such a way as to minimize the possibility of exposure of the medical personnel to microbes and to reduce the likelihood of spills and leakage of the sample. As noted below, the system described herein is closed and provides protection for the sample and the medical personnel. The unique valving and optional loss prevention media help to keep the system closed even if the sample container is inverted or tipped over accidentally during the sampling procedure.

By providing a reliable sample, this rapid system for microbial identification should allow the clinician to prescribe fewer and perhaps less initial antibiotics to the patient, thus saving toxicity to the patient, decreasing antibiotic resistance, and saving the hospital costs on unnecessary antibiotics.

In one embodiment, there is a device for sampling bodily fluids using a handle having a lumen. The distal end of the handle is adapted to connect to a sampling device which is in fluid communication with the lumen in the handle. There is also a vacuum connection on the proximal end of the handle which is also in fluid communication with the lumen in the handle. A diverter valve is located in the lumen in the handle and is used to direct a sample from a patient into a sputum trap.

In some embodiments, the sample is directed from the patient into the sputum trap by connecting the trap to the diverter valve body. In these embodiments, the flow of fluid occurs from the distal end of the device to the suction source when the trap is not attached. When the trap is attached to the valve body, the flow is diverted into the trap so that the sample may be captured. In some embodiments the trap is attached to the valve body by pushing it upwardly onto the valve body. In other embodiments the trap is attached to the valve body by inserting the valve body into the top of the trap and turning the valve body relative to the trap. Other attachment connections between the trap and the valve body involve combinations of pushing, inserting, and/or turning these respective parts.

There may be a saline port present in some embodiments to allow saline solution to be injected into the lungs of the patient to loosen and reduce the viscosity of secretions to be sampled.

A loss- or spill-prevention media may be included in the sputum trap to minimize the chance that a sample will exit the trap should the trap be inadvertently overturned. In addition, a slit, dome or other type of self-sealing valve may be used in the top of the sputum trap to help minimize the chance that a sample will spill from the trap.

BRIEF DESCRIPTION OF DRAWINGS

FIGS. 2A through 2E are illustrations of an embodiment of the handle of the device (FIG. 2A), sputum trap (FIG. 2B), a cutaway view of flow through the lumen in the handle (FIG. 2C) without a sputum trap installed, a cross-sectional view of the top of the sputum trap with a slit valve (FIG. 2D) and a cutaway view of flow with a sputum trap installed (FIG. 2E).

FIGS. 3A through 3E are illustrations of an embodiment of the handle of the device (FIG. 3A), sputum trap (FIG. 3B), a cutaway view of flow through the lumen in the handle (FIG. 3C) without a sputum trap installed, a cross-sectional view of the top of the sputum trap with a spring valve (FIG. 3D) and a cutaway view of flow with a sputum trap installed (FIG. 3E).

FIGS. 4A through 4E are illustrations of an embodiment of the handle of the device (FIG. 4A), sputum trap (FIG. 4B), a cutaway view of flow through the lumen in the handle (FIG. 4C) without a sputum trap installed, a cross-sectional view of the top of the sputum trap with a slit valve (FIG. 4D) and a cutaway view of flow with a sputum trap installed (FIG. 4E).

DETAILED DESCRIPTION

Figure 1:
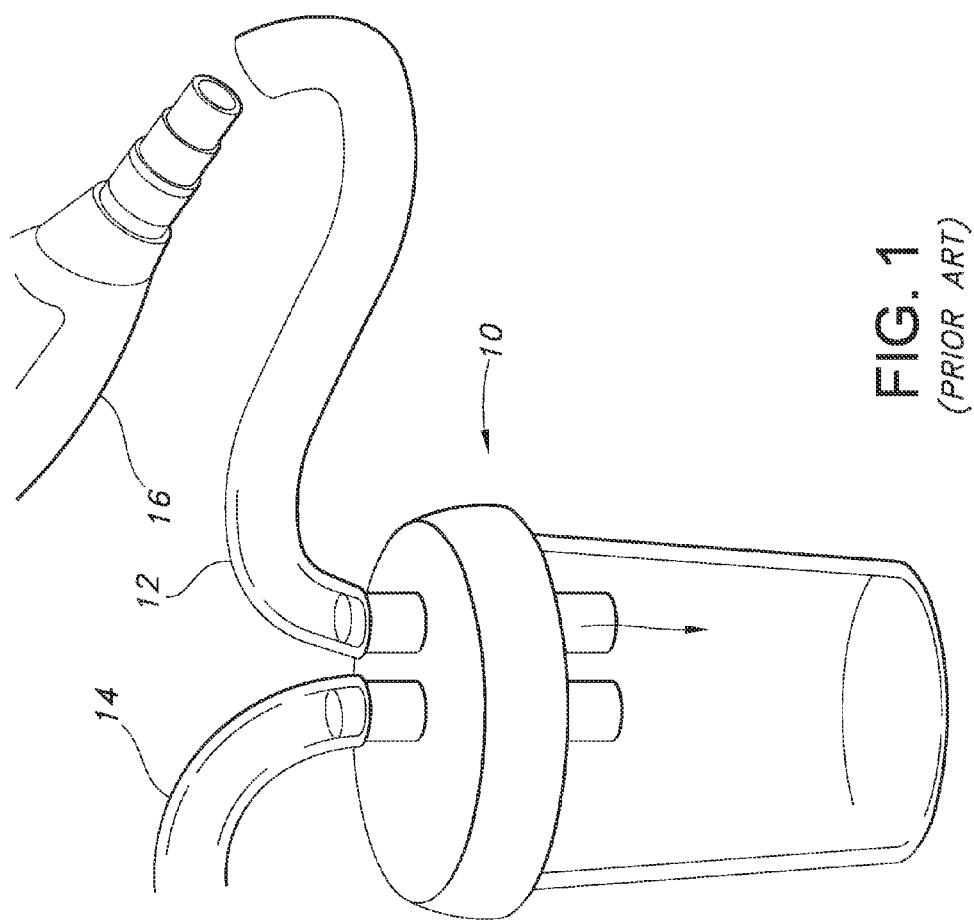
FIG. 1 is an illustration of the prior art sputum trap showing tubing entering the trap from the patient (right side) and a vacuum hose leaving on the left.

FIG. 1 shows a prior art sputum trap 10 connected by tubing 12 to a sampling device 16. Another tube 14 is connected to a standard hospital source of vacuum. As a sample is removed from a patient because of the vacuum, it is pulled through the tubing 12 to the sputum trap 10, where it falls into the trap. Negative pressure is maintained in the trap 10 by the vacuum tube 14 but the sample is not sucked out of the trap 10 because it is at the bottom of the trap 10. Should the trap 10 tip over, the sample can be sucked out of the trap 10 and lost into the hospital vacuum system, requiring re-sampling of the patient. When a sufficient amount of sample has been taken, the vacuum tube 14 is typically removed from the top of the trap 10 and the other tube 12 is removed from the device 16, bent around and connected to the top of the trap 10 where the other tube 12 had been connected to close the system. This system is prone to spillage and leakage as the tubes are removed from the various connectors and during transportation of the sputum trap 10, as noted above.

FIGS. 2A through 2E show an embodiment of the disclosed device. This embodiment has a handle 20 adapted to connect with a patient sampling device via a sampling tube 22 (shown) or directly to a distal device that may be for example, a suction catheter, a deep lung suctioning catheter, a bronchoscope, tubing or other airway suction catheter device (FIG. 2A). The handle 20 can be incorporated into, permanently attached or temporarily connected to the proximal end or suction port of one of these distal devices. A lumen 24 in the handle 20 may be in direct fluid communication with the main lumen of one of these devices. The handle 20 of this embodiment should desirably also include the following features; a saline port 26, finger suction control valve 28, vacuum port 30, and sputum trap port 32, though these are not all required.

It should be noted that the terms "distal" and "proximal" are used in their common medical usage throughout; distal being on the side closer to a patient and proximal being on the side farther away from the patient. Using this terminology, the side of a device closed to a patient is the distal side and the side farther away is the proximal side.

The saline port, if present, is in fluid communication with the lumen 24. Saline solution can be injected into the saline port 26 to rinse the tubing 22 and distal device and to rinse or dilute secretions within the patient's body to make them less viscous and easier to remove. The saline port 26 can accept a tapered luer, luer lock syringe, or a standard saline bullet. The saline port 26 desirably includes a valve, desirably a one way check valve (not shown) to close the port when a syringe is not connected in order to prevent contaminates from entering or escaping. Inserting a saline bullet opens the check valve and allows saline solution to flow into the lavage/suction lumen 24 of the handle 20. The saline port 26 is in direct communication with the handle's lavage/suction lumen 24. When the saline bullet is removed, the check valve closes, thus maintaining the integrity of the closed system.

The handle 20 desirably incorporates a finger suction control valve 28 for regulating vacuum to the distal end of the device and/or catheter. Alternatively, suction control can be incorporated into a distal device, e.g. a bronchoscope, so that a suction control valve is not needed on the handle. The valve 28 is in the normally closed position (no flow through the lumen 24) and is activated, i.e. opened for fluid flow through the lumen, upon the application of finger-induced pressure to depress the valve body 25 into the handle. Depressing the valve body 25 aligns a hole or passageway in the valve body 25 with the lumen 24, thereby allowing fluid flow through the lumen 24 and valve 28. The valve 28 automatically returns to the closed position after the user removes his finger from the valve 28, desirably by the action of a spring, though other suitable mechanisms may be used. This valve 28 could make use of a number of known mechanism designs including trumpet valves, Ballard TrachCare® thumb valves, Ballard ReadyCare® valves, etc. In this embodiment (FIG. 2A) the control valve 28 is located between the saline port 26 and sputum trap port 32. This location prevents the user from injecting saline solution directly into the sputum trap 40 when the control valve 28 is closed.

The handle 20 also incorporates a male vacuum port 30 to which standard vacuum tubing used in the typical hospital can attach. The vacuum port 30 is in communication with the lumen 24. The handle 20 is designed to be used with a continuous vacuum sources supplied by the hospital or by portable vacuum units.

The handle 20 also has a sputum trap port 32 where a sputum trap 40 (FIG. 2B) can be securely attached via, for example, a circular luer twist attachment 34. Other attachment methods could include standard friction fit (with or without o-ring), snaps, etc. A single port 32 design that is desirably circular, allows the user to intuitively connect the trap blindly; requires no lining up of multiple holes, slides, etc. No covers or slides need to be opened or closed on the handle 20 prior to connecting the sputum trap 40. The sputum trap port 32 is a part of the diverter valve 36 and contains lumen 50, 52 for fluid communication with the sputum trap 40. It is desirable that the lumens 50, 52 are recessed above the end of the sputum trap port 32 when the handle 20 is not connected to a sputum trap 40 in order to minimize the likelihood of contact with secretions by the medical personnel.

The handle 20 functions with or without a sputum trap 40 attached. The handle 20 in this embodiment incorporates a diverter valve 36 within the handle 20 which allows flow from the patient either directly towards the vacuum port 30 or into the sputum trap 40 when the trap 40 is attached. When the sputum trap 40 is not attached, the diverter valve 36 does not block the lumen 24 because valve 36 is pushed out of the way by a spring 38 or other mechanism like a coil, leaf, or elastic material etc. (FIG. 2C). When the suction control valve 28 is activated (i.e. depressed), suction is applied to the patient sampling tube 22 (on the distal end) from the vacuum port 30 because fluid communication between the tube 22 and vacuum port 30 is established. When a sputum trap 40 is connected the diverter valve 36 is pushed upwards into the diverter valve body 35 by the sputum trap 40, compressing the spring 38 and diverting the flow in the lumen 24 into a first diverter lumen 50 leading downwards into the sputum trap port 32 and into the sputum trap 40. A second diverter lumen 52 is in communication with the vacuum port 30. The distal end of the two lumens 50, 52 are desirably offset a sufficient distance so that the sample does not get vacuumed into the second lumen 52 but is allowed to drop via gravity into the sputum trap 40. When the sputum trap 40 is removed the diverter valve 36 returns to its original position in the diverter valve body 35 because of the action of the spring 38, blocking flow in the lumens 50, 52 to the sputum trap 40 and re-establishing the direct fluid connection between the sampling tube 22 and the vacuum port 30.

The sputum trap 40 is spill resistant when it is not connected to the sputum trap port 32 via a self-sealing valve 46 incorporated into the sputum trap cap 44. Such spill resistant means could be a slit-type or "slit" valve 46 as shown in FIGS. 2B, 2D and 2E. FIG. 2D is a cross-sectional view of the cap 44 and slit valve 46 showing the slit valve 46 in the closed position. FIG. 2E shows the slit valve 46 in the open position when the diverter valve 36 pushes open the slit valve 46. The slit valve 46 returns to the closed position when the diverter valve 36 is removed. Slit valves are commercially available from LMS Inc. (Liquid Molding Systems Inc., a subsidiary of Aptar Group Inc.) of Midland Mich., and may be made from medical grade silicon.

Another type of spill resistant means that could be used is shown in FIGS. 3B, 3D and 3E and is a spring loaded valve 60. When the diverter valve 36 is inserted into the sputum trap 40, the spring valve 60 is pressed downward, establishing a channel between the sampling tube 22 and the sputum trap 40 (FIG. 3E). Upon withdrawal of the diverter valve 36 the spring valve 60 closes the top of the sputum trap 40 (FIG. 3C).

The entire sputum trap cap 44 may be removed in a manner similar to prior art sputum traps. This allows lab techs to easily access the sample within according to known procedures. A secondary cap 42 can be attached to the sputum trap cap 44 for use for long term storage or shipping/handling to the lab for extra security and confidence. The secondary cap 42 desirably fits into the cap 44 where the handle sputum trap port 32 has been removed.

Another embodiment (FIGS. 4A through 4E) shows a combination suction and diverter control valve 54 in place of the diverter valve 36. The separate suction valve 28 is not present in this embodiment. Without a sputum trap 40 in place, the combination valve 54 functions in the same manner as the suction control valve 28 of previous embodiments; i.e., it regulates vacuum to the distal end of the device and/or catheter in response to the depression of the valve by the finger. The valve 54 is in the normally closed position (no flow through the suction/lavage lumen 24) and automatically returns to the closed position after the user removes his finger from the valve 54, just as the separate suction control valve 28 functions.

When a sputum trap 40 is attached to the handle 20 of the embodiment of FIG. 4A, the diverter valve 36 portion of the combination valve 54 is moved upwardly, aligning the lumen 24 with the diverter lumens 50, 52. Suction through the lumen is still blocked however. When the sputum trap 40 is attached to the valve body 35 and the combination valve 54 pushed down (FIG. 4E), suction is established through the valve 54, diverting the flow in the lumen 24 into a first lumen 50 leading downwards into the sputum trap port 32 and into the sputum trap 40. A second lumen 52 is in communication with the sputum trap 40 and the vacuum port 30. The distal end of the two lumens 50, 52 are desirably offset a sufficient distance so that the sample does not get vacuumed into the second lumen 52 but is allowed to drop via gravity into the sputum trap 40.

Figure 5:
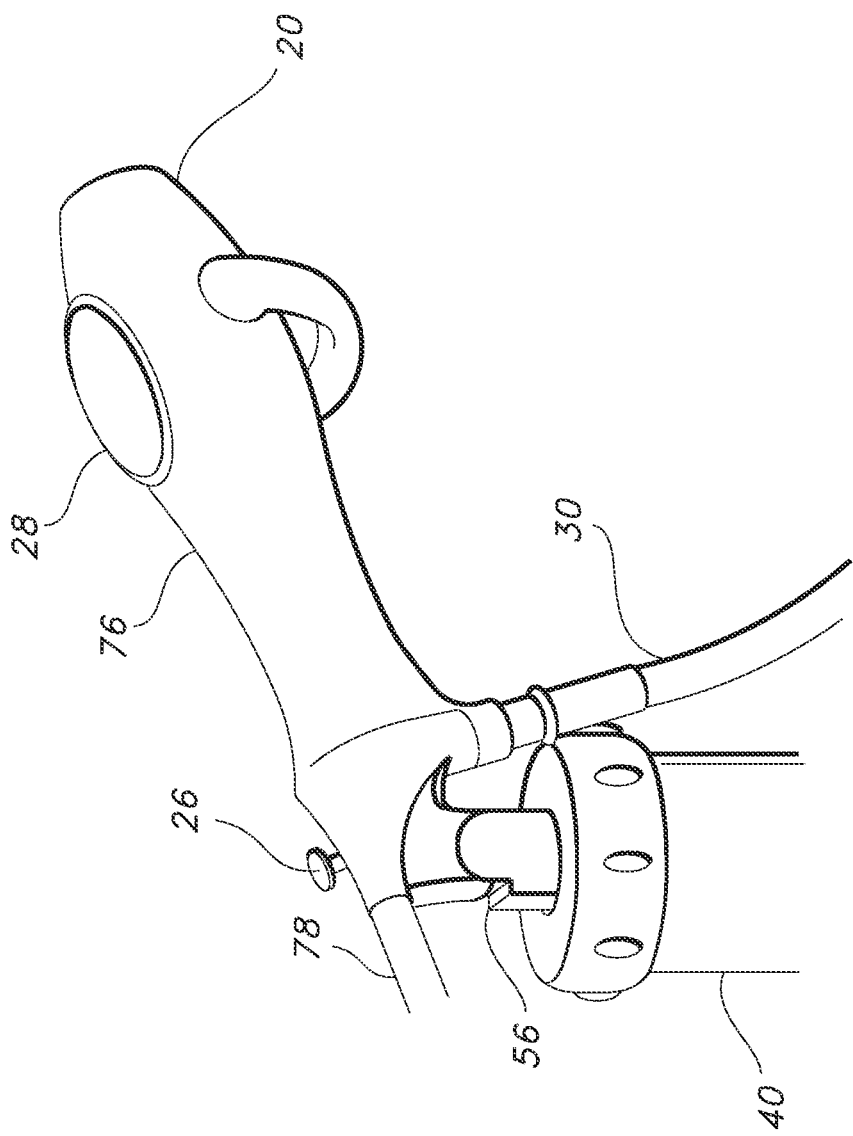
FIG. 5 is an illustration of a bronchoscope incorporating the sampling device disclosed herein. The bronchoscope has an eyepiece through which the user views the location of the end of the bronchoscope tube. When the suction valve is depressed, suction is applied to the bronchoscope tube and secretions are suctioned into the sputum trap.

In still another embodiment, FIG. 5 shows the disclosed sampling device with the further incorporation of a bronchoscope 76. The bronchoscope 76 has an eyepiece 70 through which the user views the location of the end of the bronchoscope tube 78. In this embodiment a swivel 56 is placed between the handle 20 and the sputum trap 40 in order to keep the sample in the sputum trap 40 level during manipulation of the bronchoscope 76. When the suction valve 28 is depressed, suction is applied to the bronchoscope tube 78 through the vacuum port 30 and secretions are suctioned into the sputum trap 40. A saline port may 26 also be included in this embodiment if desired and will function in the same manner as in the other embodiments.

Figure 6C:
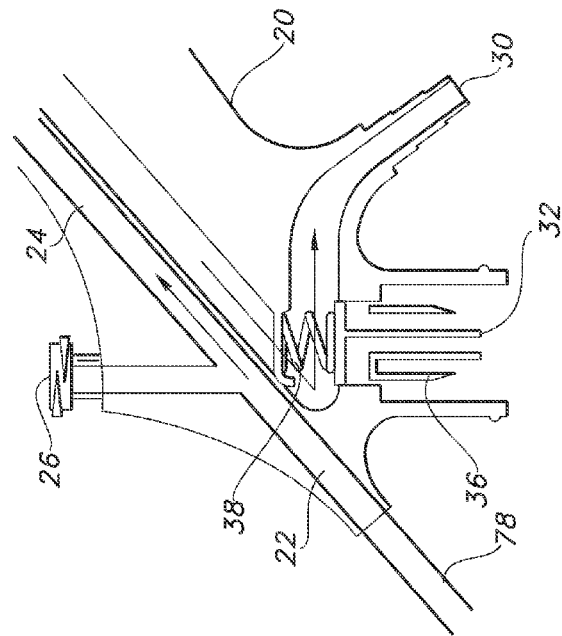
FIG. 6A through 6D are illustrations of an embodiment of a bronchoscope incorporating the sampling device disclosed herein (FIG. 6A). There is a cutaway view of a lumen in the handle (FIG. 6B), a cross-sectional view of the handle in the area of the diverter valve (FIG. 6C) and a cross-sectional view of the top of the sputum trap with a slit valve (FIG. 6D).
Figure 6D:
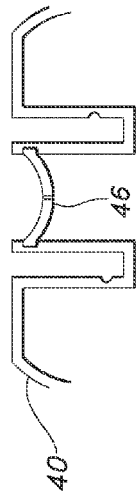
Figure 6B:
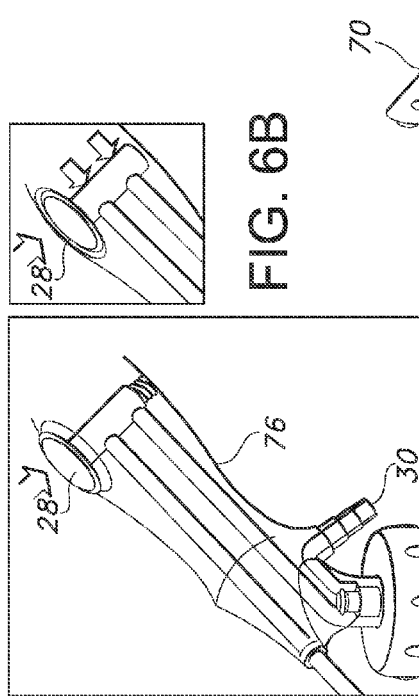
Figure 6A:
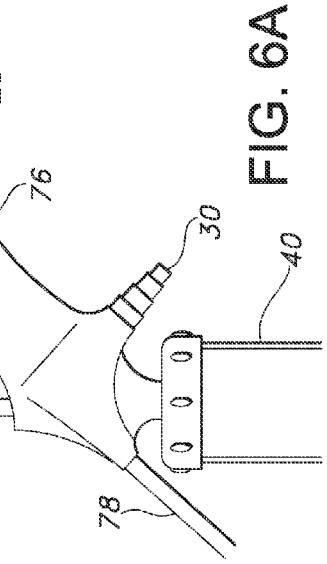

FIGS. 6A through 6D provides additional views of the bronchoscope 76 incorporating the disclosed sampling device. The diverter valve 36 is shown in a cross-sectional view of the handle (FIG. 6C). FIG. 6B shows the action of the suction control valve 28 when it is depressed and not depressed, showing the alignment of the lumens and completion of the suction circuit when the valve is depressed. This view also illustrates the location of the saline port 26 (FIGS. 6A and 6D). The embodiment of FIG. 6 does not have a swivel 56 connection between the bronchoscope 76 and the sputum trap.

Figure 7A:
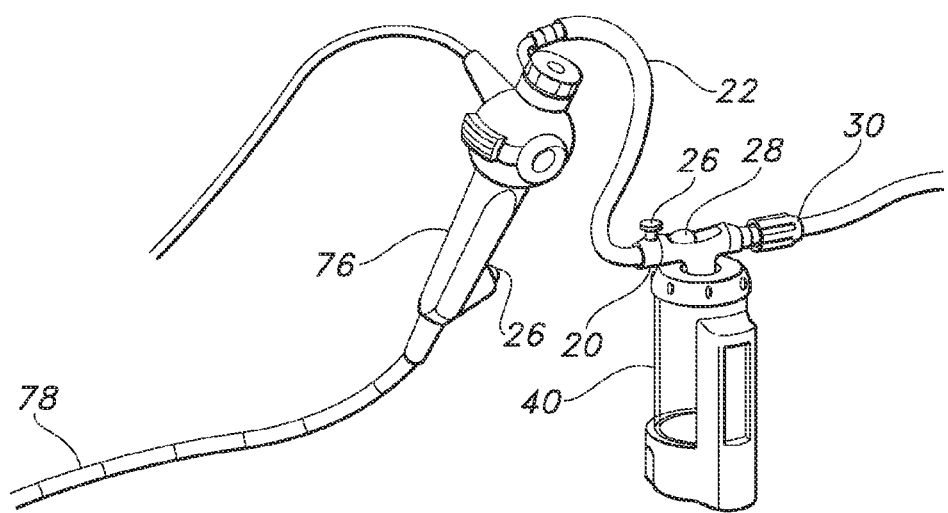
FIG. 7A is an illustration of an embodiment of the handle(s) described in FIGS. 2A through 4E and used in conjunction with a bronchoscope.
Figure 7B:
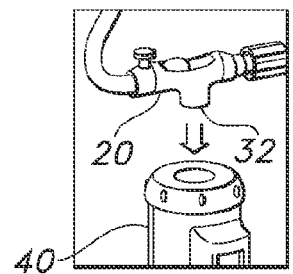
FIG. 7B shows the connection of the sputum trap to the diverter valve and handle.

In FIG. 7A, the handle 20 described for FIGS. 2 through 4 is connected to a standard bronchoscope 76 via standard tubing 22. In this embodiment the handle 20 is not directly connected to the sampling catheter (i.e. bronchoscope tube 78) though it is still in fluid communication with the suction channel of the bronchoscope. This arrangement can also be used with any open suction or closed suctioned catheter commonly used during medical care.

Figure 8A:
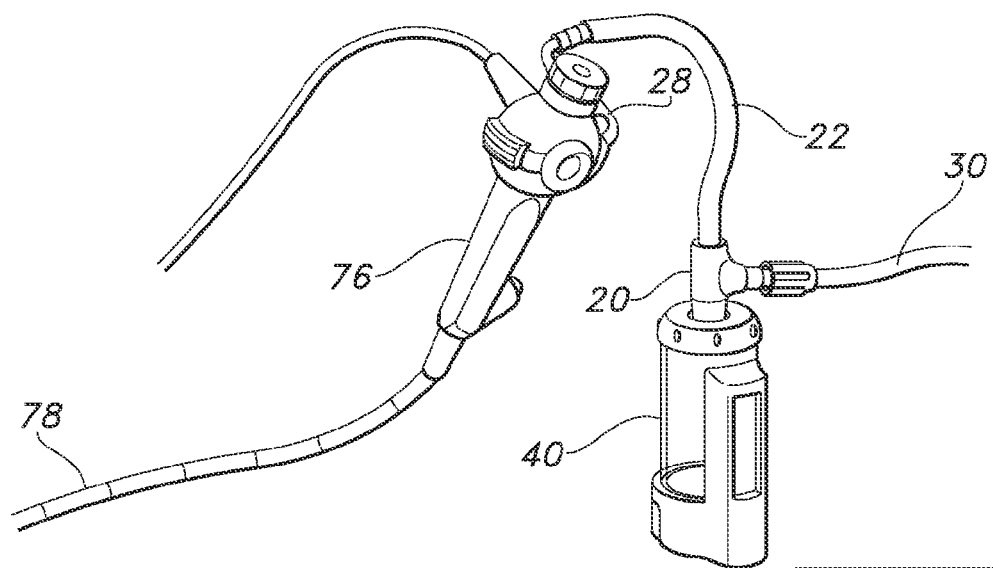
FIG. 8A is an illustration of an embodiment of a handle used in conjunction with a bronchoscope.
Figure 8B:
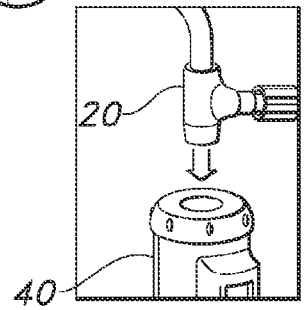
FIG. 8B shows the connection of the sputum trap and the handle of the diverter valve.

In FIG. 8, the handle 20 has similar features to those of the handles shown in FIGS. 2 through 4, but excluding the optional suction control function or a port for saline addition. The handle 20 does maintain the ability to quickly attach and detach a sputum trap 40 while keeping the system closed and without disconnecting tubing from or to the distal device; bronchoscope, suction catheter, sampling catheter, etc. Note that the suction control valve is excluded from the handle 20 in this embodiment since may bronchoscopes already include a suction control means, though it is not visible in this Figure. In this instance the handle 20 functions more like an adapter to attach the trap 40 to the bronchoscope 76 system.

Figure 9:
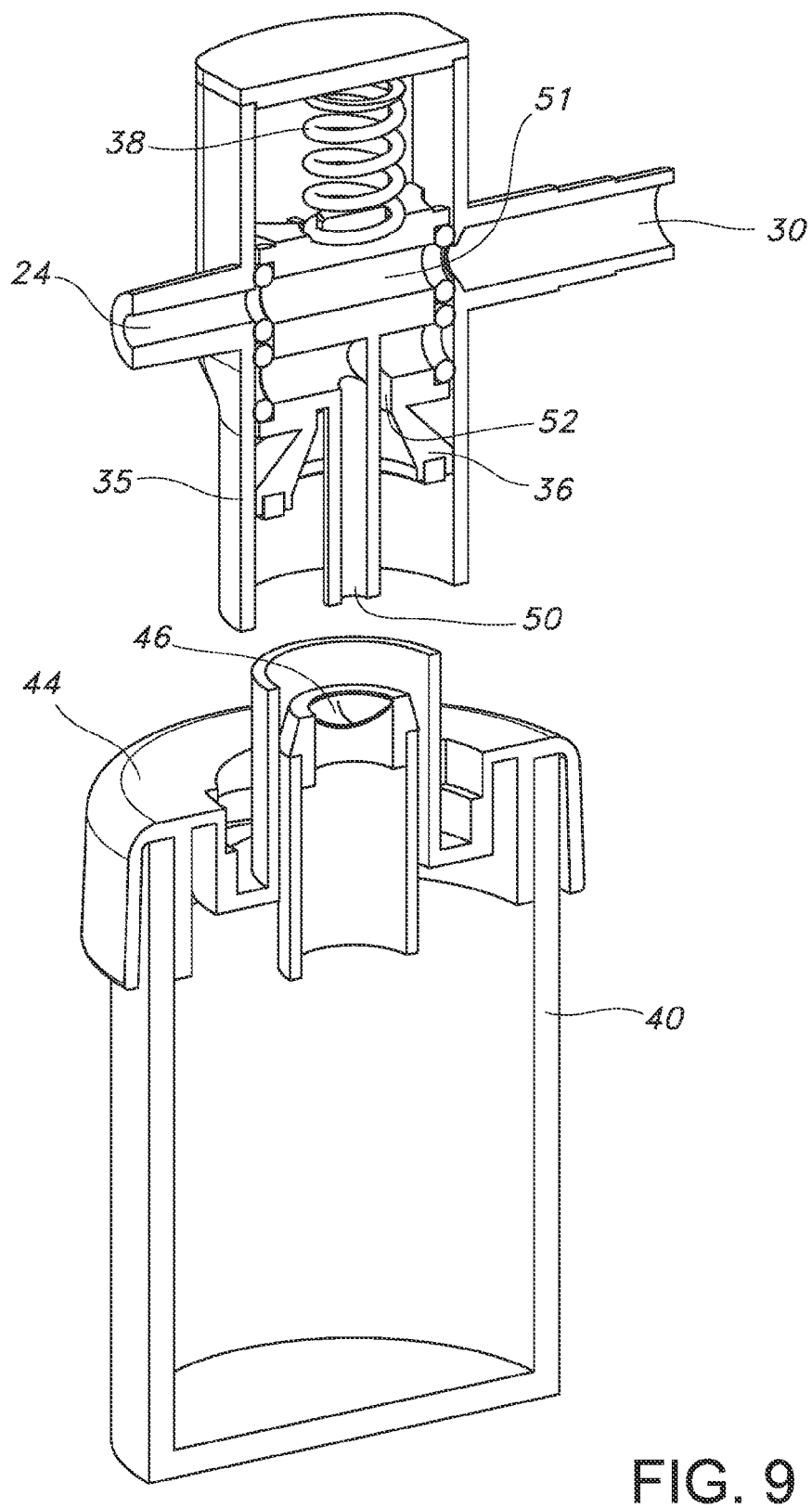
FIG. 9 is an illustration of an embodiment in which the diverter valve does not block fluid communication between the distal end of the lumen and the vacuum source because it is pushed out of the way by a spring or other mechanism like a coil, leaf, or elastic material etc.
Figure 10:
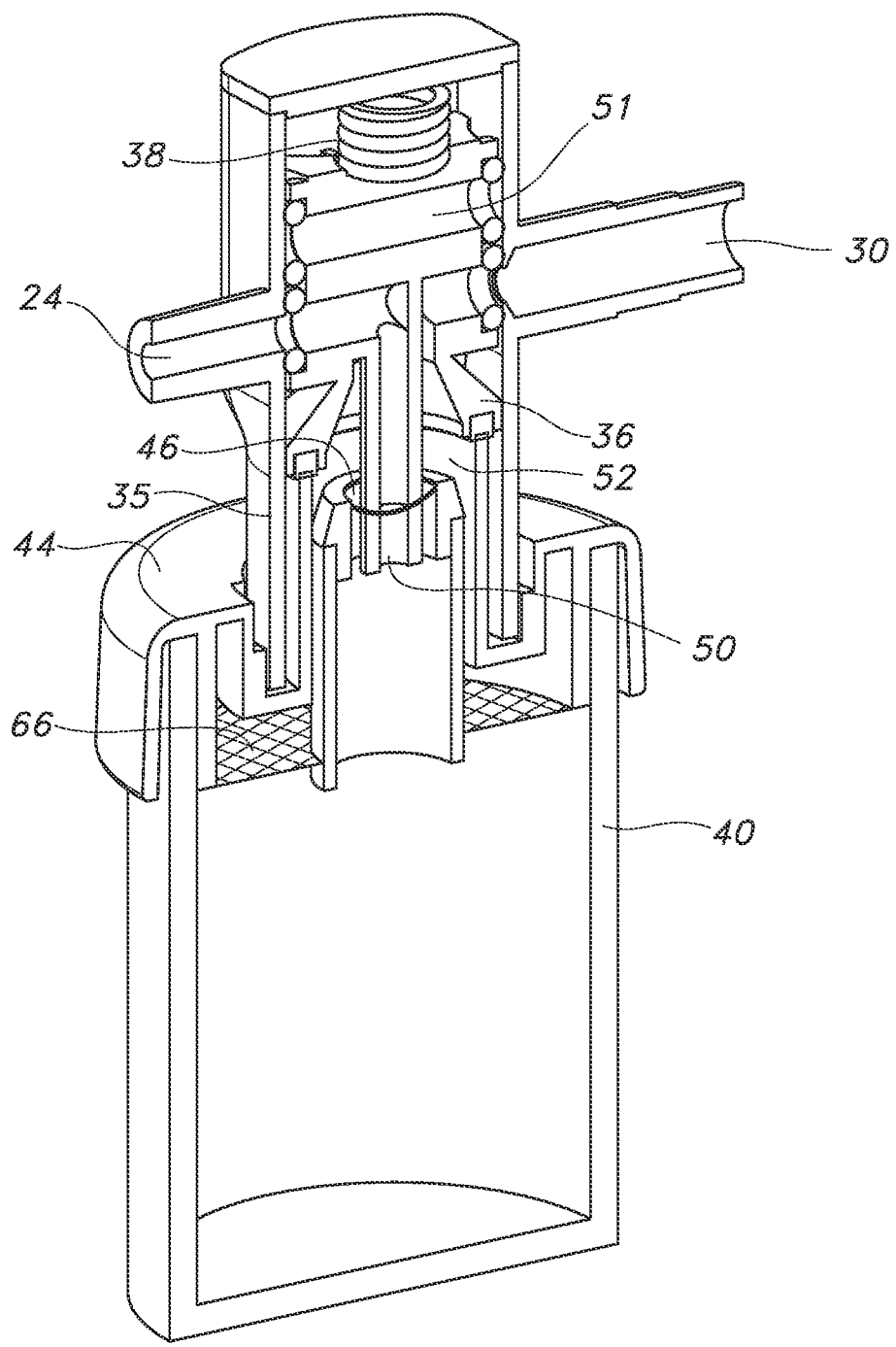
FIG. 10 is an illustration of the embodiment of FIG. 9 in which the diverter valve is pushed upwards in the valve body by the sputum trap cap, compressing the spring and diverting the flow in the lumen into a first diverter lumen 50 leading downwards into the sputum trap so that a sample may be captured.

FIGS. 9 and 10 show another embodiment that does not require push button activation. In this embodiment the diverter valve 36 allows flow to occur from the distal end of the device to the suction source when the trap 40 is not attached to the diverter valve body 35. When the sputum trap cap 44 is not attached (FIG. 9), the diverter valve 36 does not block fluid communication between the lumen 24 and the vacuum port 30 through the diverter valve lumen 51 because it is pushed out of the way by a spring 38 or other mechanism like a coil, leaf, or elastic material etc. Turning to FIG. 10, it can be seen that when the sputum trap cap 44 is attached to the diverter valve body 35, the diverter valve 36 is pushed upwards by the sputum trap cap 44, compressing the spring 38 and diverting the flow through lumen 24 into a first diverter lumen 50 leading downwards into the sputum trap 40. A second diverter lumen 52 is in fluid communication with the vacuum port 30. The distal ends of the two lumens 50, 52 are desirably offset a sufficient distance so that the sample does not get vacuumed into the second lumen 52 but is allowed to drop via gravity into the sputum trap 40. When the sputum trap 40 is removed from contact with the diverter valve body 35, the diverter valve 36 returns to its original position because of the action of the spring 38, blocking flow in the lumens 50, 52 to the sputum trap 40 and re-establishing the direct fluid connection between the suction/lavage lumen 22 and the vacuum port 30 through the diverter valve lumen 51.

FIG. 10 also shows a loss prevention media 66 in position at the upper part of the sputum trap 40 or lower part of the cap 44, desirably on only the suction lumen 52 side of the air flow. The loss prevention media 66 helps to keep the sample in the trap 40 if the trap is dropped or tipped over and may be attached by, for example, sonic bonding, to the cap 44 or trap 40. The loss prevention media is desirably breathable or air permeable and may be a nonwoven fabric or a breathable film or a combination thereof. The media 66 remains stable when suction is applied to the trap 40. A suitable material may be a nonwoven fabric between for example, 0.5 and 3.0 osy (17 and 102 gsm). The fabric may be a spunbond or meltblown fabric or a laminate having various layers of spunbond and meltblown fabric. The fabric is desirably hydrophobic, i.e. having a contact angle of greater than 90 degrees and desirably has an average pore size of about 25 microns, though this is not meant as a limitation but merely as guidance for the skilled practitioner. Suitable nonwoven fabric materials include polyolefins like polyethylene and polypropylene as well as nylons and urethanes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

Figure 11:
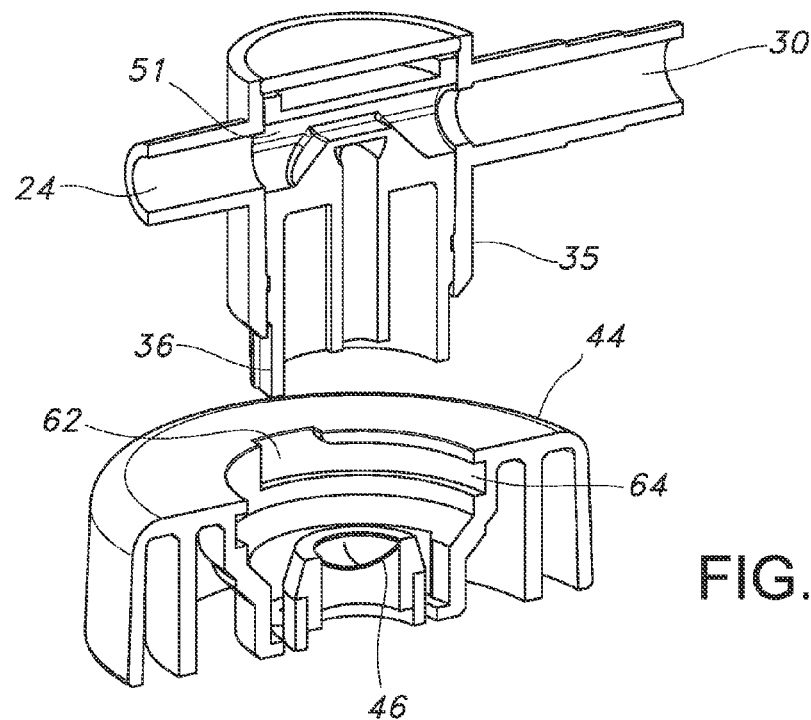
FIG. 11 is an illustration of an embodiment that does not require push button activation. In this Figure the diverter valve 36 allows flow to occur from the distal end of the device to the suction source when the sputum trap is not attached.
Figure 12:
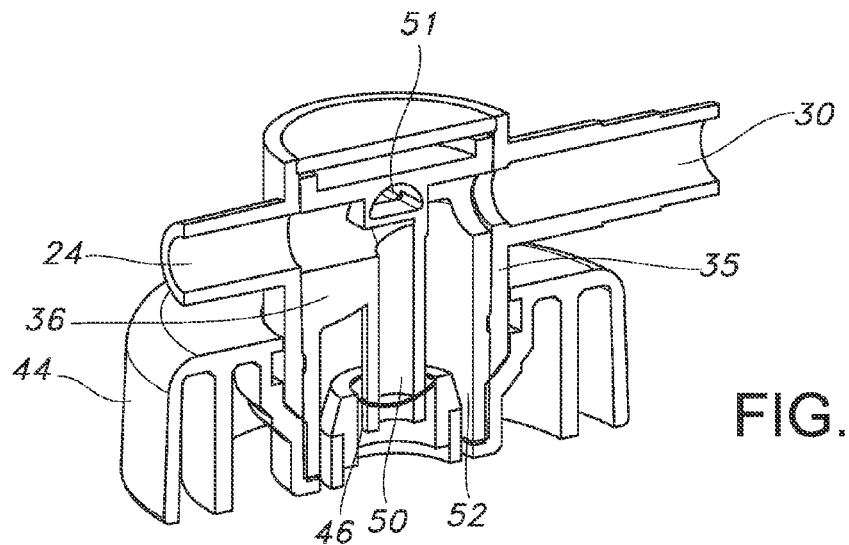
FIG. 12 is an illustration of the embodiment of FIG. 11 in which, when the sputum trap cap is attached to the diverter valve body and turned, the diverter valve is rotated within the diverter valve body, diverting the flow in the lumen into a first diverter lumen leading downwards into the sputum trap.
Figure 13:
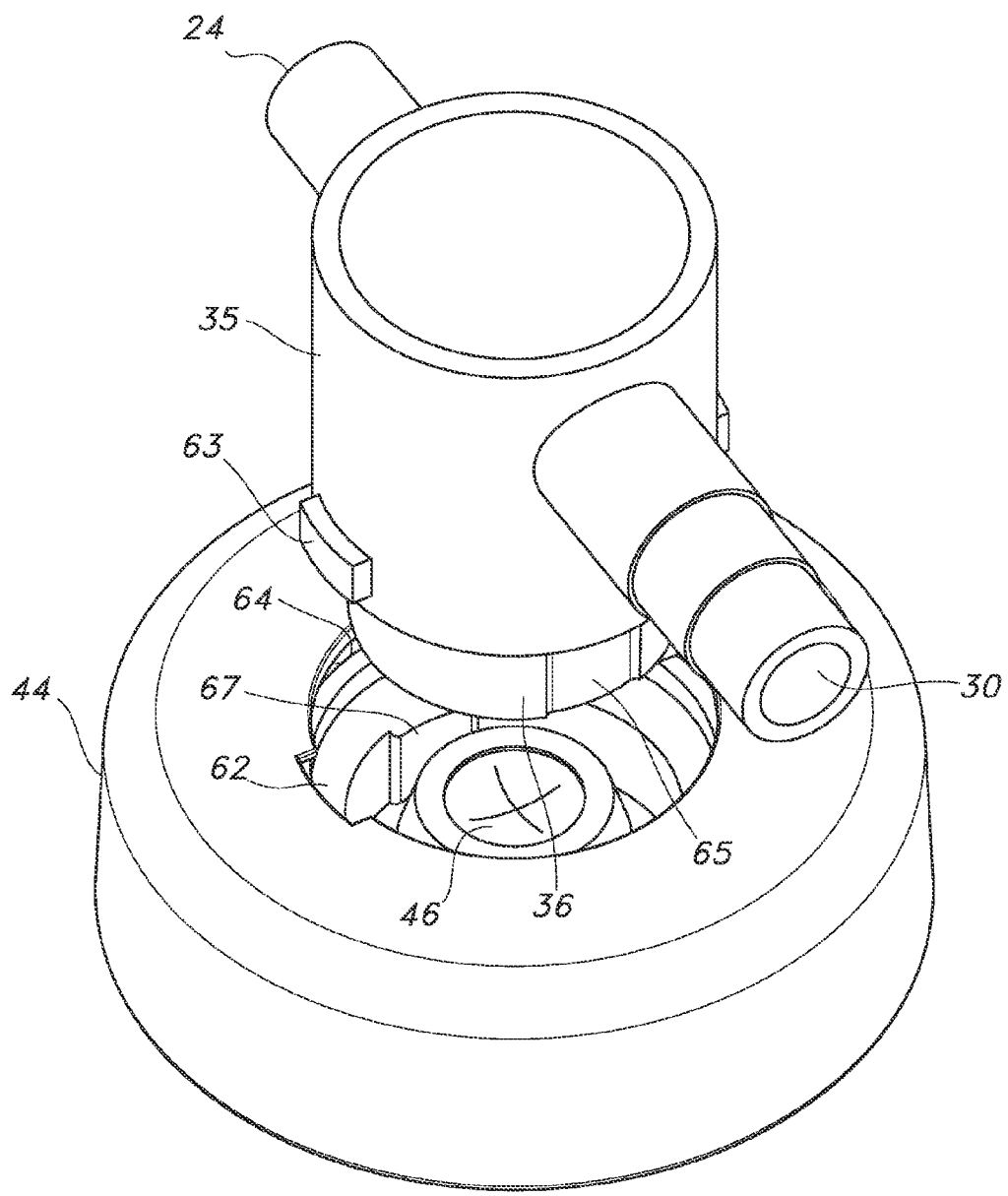
FIG. 13 is an illustration of the embodiment of FIGS. 11 and 12 which more clearly shows how the diverter valve body is "keyed" into the sputum trap cap by tabs on either side of the body, and once inserted into the key opening, may be turned by approximately 90 degrees in the keyway. This view also shows that when the diverter valve body is turned in the keyway, the diverter valve remains stationary relative to the sputum trap because the diverter valve is keyed into the cap by tabs on the cap and matching slots on either side of the diverter valve.

FIGS. 11, 12 and 13 show another embodiment that does not require push button activation. In this embodiment the diverter valve 36 allows flow to occur from the distal end of the device to the suction source when the trap 40 is not attached. When the sputum trap cap 44 is not attached (FIG. 11), the diverter valve 36 does not block fluid communication between the suction/lavage lumen 24 and the vacuum port 30 through the diverter lumen 51.

As shown in FIG. 13 the diverter valve body 35 in this embodiment is "keyed" into the sputum trap cap 44 by tabs 63 on either side of the body 35, and once inserted into the key opening 62, may be turned by approximately 90 degrees in the keyway 64. When the diverter valve body 35 is turned in the keyway 64, the diverter valve 36 remains stationary relative to the sputum trap 40 because the diverter valve 36 is keyed into the cap 44 by tabs 67 on the cap 44 and matching slots 65 on either side of the diverter valve 36. The tabs 63 also serve to keep the valve attached to the sputum trap once the valve body 35 is turned in the keyway 64, helping to avoid spilling the sample. Alternate methods of allowing the valve body 35 to turn relative to diverter valve 36 may also be used.

Turning to FIG. 12, it can be seen that when the sputum trap cap 44 is attached to the diverter valve body 35 and turned, the diverter valve 36 is rotated within the diverter valve body 35, diverting the flow in the suction/lavage lumen 24 into a first diverter lumen 50 leading downwards into the sputum trap 40. A second diverter lumen 52 is in fluid communication with the vacuum port 30. The distal ends of the two lumens 50, 52 are desirably offset a sufficient distance so that the sample does not get vacuumed into the second lumen 52 but is allowed to drop via gravity into the sputum trap 40. When the sputum trap 40 is removed by turning it in the reverse direction an equivalent distance, the diverter valve 36 returns to its original position within the diverter valve body 35, blocking flow in the lumens 50, 52 to the sputum trap 40 and re-establishing the direct fluid connection between the lumen 24 and the vacuum port 30 through the diverter lumen 51 (FIG. 11). The diverter valve 36 within the diverter valve body 35 may be removed from the sputum trap cap 44 by moving them apart to remove the diverter valve and body from the key opening 62 in the sputum trap cap 44.

It should be clear that some of the embodiments contain a valve having a first position in which a distal end of the valve is in fluid communication with a source of vacuum and a second position in which the distal end of the valve is in fluid communication with a sputum trap and the sputum trap is in fluid communication with the source of vacuum. The diverter valve in these embodiments may be moved from the first position to the second position by the connection of the sputum trap to the valve body In the use of the disclosed device, once the sampling tube 22 (or its associated distal device as discussed above) is inserted into the desired location (desirably below the corina, ideally in the third generation lung lobe), saline solution may be injected via the saline port 26 and allowed to travel into the patient's respiratory tract. Suction may be applied by depressing the suction valve 28 to remove the secretions from the patient. If it is desired to capture the secretions, a sputum trap 40 can be connected to the sputum trap port 32 and suction applied thereafter by depressing the suction valve 28. A sample of the secretions is then diverted into the sputum trap 40 for collection. Once sufficient sample has been collected, the sputum trap 40 may be disconnected, automatically closing it, and the trap 40 sent to a lab for analysis.

The sample may also desirably be analyzed while it is still in the sputum trap. This procedure would provide a more immediate result than sending a sample to a lab located some distance from the patient. Such a result would potentially have cost advantages because proper (i.e. more targeted) antibiotics could be administered to the patient earlier in his treatment.

The valve, handle and sputum trap may be made from plastics like polyolefins and nylon. The sputum trap is desirably transparent so that the user may see if a sample has been collected.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

We claim:

1. A diverter valve for taking a sample from a patient, said diverter valve comprising:
a valve body containing a valve comprising a first diverter lumen and a second diverter lumen, said valve having a first position in which a distal end of said valve is in fluid communication with a source of vacuum and a second position in which said distal end of said valve is in fluid communication with a sputum trap via said first diverter lumen and said sputum trap is in fluid communication with said source of vacuum via said second diverter lumen, wherein said valve is moved from said first position to said second position by the connection of said sputum trap to said valve body by twisting said valve body in a keyway in said sputum trap.

2. The diverter valve of claim 1 further comprising a loss prevention media in said sputum trap to prevent said sample from escaping.

3. The diverter valve of claim 2 wherein said loss prevention media is a nonwoven fabric, breathable film, or combination thereof.

* * * * *